(12) United States Patent
Labrie et al.

(10) Patent No.: US 6,204,372 B1
(45) Date of Patent: Mar. 20, 2001

(54) DNA ENCODING A HUMAN TUBBY HOMOLOG

(75) Inventors: Samuel T. Labrie, Mountain View; Preeti Lal, Sunnyvale; Lynn E. Murry, Portola Valley, all of CA (US)

(73) Assignee: Incyte Genomics, Inc., Palo Alto, CA (US)

(*) Notice: Subject to any disclaimer, the term of this patent is extended or adjusted under 35 U.S.C. 154(b) by 0 days.

(21) Appl. No.: 08/812,824

(22) Filed: Mar. 6, 1997

(51) Int. Cl.$^7$ .............................. C12N 15/00; C12N 15/09
(52) U.S. Cl. .................... 536/23.5; 536/23.51; 536/243; 435/69.1; 435/69.4; 435/69.5; 435/6; 435/252.3; 435/320.1
(58) Field of Search .................. 536/23.5, 24.3, 536/23.51; 435/69.1, 69.5, 320.1, 252.3, 6, 69.4

(56) References Cited

U.S. PATENT DOCUMENTS 5,646,040 * 7/1997 Kleyn et al. ..................... 435/325
6,114,502 * 9/2000 North et al. ..................... 530/350

FOREIGN PATENT DOCUMENTS

WO 97/02048   1/1997   (WO).

OTHER PUBLICATIONS

Coleman, DL and Eicher, EM, "Fat (fat) and tubby (tub): two autosomal recessive mutations causing obesity syndromes in the mouse" *J Hered* 81 (6):424–427 (1990).
Noben–Trauth, K et al., "A candidate gene for the mouse mutation tubby" *Letters to Nature* 380:534–538 (1996) (GI 1279766).
Kleyn, PW et al., "Indentification and Characterization of the Mounse Obesity Gene tubby: A Member of a Novel Gene Family" *Cell* 85:281–290 (1996) (GI 1305497).
Database EMBL—EMSTS, Entry HS615299, Acc. No. G17615, Mar. 7, 1996, Myers, R.M.: "human STS SHGC–1217 clone pg–71".

* cited by examiner

*Primary Examiner*—Garnette D. Draper
(74) *Attorney, Agent, or Firm*—Incyte Genomics, Inc.

(57) ABSTRACT

The present invention provides a novel human tubby homolog (NHT) and polynucleotides which identify and encode NHT. The invention also provides expression vectors, host cells, agonists, antibodies, or antagonists. The invention also provides methods for treating disorders associated with appetite and eating.

9 Claims, 8 Drawing Sheets

FIGURE 1A

```
5' NGC ACG AGG TGG GGG CTT TCC TCG GCG GGC ATG GAG GCT TCG CGC TGC CGG        54
         T   R   W   G   L   S   S   A   G   M   E   A   S   R   C   R

CTC AGT CCC AGC GGC GAC AGT GTC TTC CAT GAA GAA ATG AAG ATG CGA CAG       108
    L   S   P   S   G   D   S   V   F   H   E   E   M   K   M   R   Q

GCT AAG CTG GAT TAT CAG AGG CTA CTT GAG AAG AGG CAA AAA AAG CGC           162
    A   K   L   D   Y   Q   R   L   L   E   K   R   Q   K   K   R

CTT GAG CCA TTT ATG GTG CAG CCC AAT CCA GAA GCC AGG CTA CGT CGG GCA AAG   216
    L   E   P   F   M   V   Q   P   N   P   E   A   R   L   R   R   A   K

CCA AGG GCC AGT GAT GAG CAG ACT CCC TTG GTG GCT GTC CTG AAC TGT CAT AGC   270
    P   R   A   S   D   E   Q   T   P   L   V   A   V   L   N   C   H   S

AAT GTC ATC TTA CAT GGT ATT GAT GCT GGT CCA GCT GTC CTG AAA CCA GAC GAA   324
    N   V   I   L   H   G   I   D   A   G   P   A   V   L   K   P   D   E

GTT CAT GCT CCA TCA GTA AGC TCC TCT GTT GTG GAA GAA GAT GCT GAA AAC ACC   378
    V   H   A   P   S   V   S   S   S   V   V   E   E   D   A   E   N   T
```

```
     387         396     405     414     423     432
GTG GAT ACT GCT TCC AAG CCA GGA CTT CAG GAG CGT CTC CAA AAG CAT GAT ATC
 V   D   T   A   S   K   P   G   L   Q   E   R   L   Q   K   H   D   I
     441         450     459     468     477     486
TCT GAA AGT GTG AAC TTC GAT GAG ACT GAT GGA ATA TCC CAG TCA GCA TGT
 S   E   S   V   N   F   D   E   T   D   G   I   S   Q   S   A   C
     495         504     513     522     531     540
TTA GAA AGA CCC AAT TCT GCA TCA AGC CAG AAT TCA ACC GAT ACA GGC ACT TCC
 L   E   R   P   N   S   A   S   S   Q   N   S   T   D   T   G   T   S
     549         558     567     576     585     594
GGT TCT GCT ACT GCC GCC CAA CCA GCT GAT AAC CTC CTG GGA GAC ATA GAC GAC
 G   S   A   T   A   A   Q   P   A   D   N   L   L   G   D   I   D   D
     603         612     621     630     639     648
CTG GAG GAC TTT GTG TAT AGT CCT GCC CCT CAA GGT GTC ACA GGT AGA TGT CGG
 L   E   D   F   V   Y   S   P   A   P   Q   G   V   T   G   R   C   R
     657         666     675     684     693     702
ATA ATC CGG GAT AAA AGG GGA ATG GAT CGG GGT CTC TTC CCC ACC TAC TAT ATG
 I   I   R   D   K   R   G   M   D   R   G   L   F   P   T   Y   Y   M
     711         720     729     738     747     756
TAC TTG GAA AAA GAA GAA AAT CAG AAG ATA TTT CTT CTT GCA GCT AGA AAG CGG
 Y   L   E   K   E   E   N   Q   K   I   F   L   L   A   A   R   K   R
```

FIGURE 1B

```
       765           774           783           792           801           810
AAA AAG AGC AAA ACA GCC AAC TAC CTT ATC TCC ATT GAT CCA GTT GAT TTA TCT
 K   K   S   K   T   A   N   Y   L   I   S   I   D   P   V   D   L   S 819           828           837           846           855           864
CGT GAA GGA GAA AGT TAT GTC GGC AAG CTT AGA TCC AAC CTC ATG GGG ACC AAG
 R   E   G   E   S   Y   V   G   K   L   R   S   N   L   M   G   T   K 873           882           891           900           909           918
TTT ACA GTT TAT GAC CGT GGC ATC TGC CCC ATG AAG GGC CGG GGT TTG GTA GGA
 F   T   V   Y   D   R   G   I   C   P   M   K   G   R   G   L   V   G 927           936           945           954           963           972
GCG GCC CAC ACC CGG CAG GAG CTG GCT GCC ATC TCC TAT GAA ACA AAC GTA CTT
 A   A   H   T   R   Q   E   L   A   A   I   S   Y   E   T   N   V   L 981           990           999          1008          1017          1026
GGA TTT AAA GGT CCT AGG AAA ATG TCT GTG ATC ATT CCT GGA ATG ACA CTG AAT
 G   F   K   G   P   R   K   M   S   V   I   I   P   G   M   T   L   N 1035          1044          1053          1062          1071          1080
CAT AAG CAG ATC CCC TAT CAG CCA CAA AAC AAC ATT GAC AGT TTG CTC TCA AGG
 H   K   Q   I   P   Y   Q   P   Q   N   N   I   D   S   L   L   S   R 1089          1098          1107          1116          1125          1134
TGG CAG AAC AGA ACT ATG GAA AAT CTG GTT GAG CTG CAC AAC AAG GCC CCC GTC
 W   Q   N   R   T   M   E   N   L   V   E   L   H   N   K   A   P   V
```

FIGURE 1C

```
TGG AAC AGT GAC ACT CAG TCC TAT GTC CTC AAC TTC CGT GGC CGG GTC ACT CAG
 W   N   S   D   T   Q   S   Y   V   L   N   F   R   G   R   V   T   Q
1143        1152        1161        1170        1179        1188

GCG TCT GTG AAG AAC TTC CAG ATA GTC CAC AAA AAT GAC CCT GAT TAT ATA GTC
 A   S   V   K   N   F   Q   I   V   H   K   N   D   P   D   Y   I   V
1197        1206        1215        1224        1233        1242

ATG CAG TTT GGA CGT GTG GCA GAT GAC GTG TTC ACA CTG GAT TAC AAC TAC CCA
 M   Q   F   G   R   V   A   D   D   V   F   T   L   D   Y   N   Y   P
1251        1260        1269        1278        1287        1296

CTT TGT GCA GTA CAG GCC ATC GGT CTT TCT AGC TTT GAC AAA CGT ATC
 L   C   A   V   Q   A   I   G   L   S   S   F   D   K   R   I
1305        1314        1323        1332        1341        1350

CAA ACC TTG AGA ATG CAG GAG CTC TGT GAG CTC CAC CGT CAG CAC CAT TCA GCT
 Q   T   L   R   M   Q   E   L   C   E   L   H   R   Q   H   H   S   A
1359        1368        1377        1386        1395        1404

GCA TCC CTT GTG CAC AGG ACT GCC TGC CAG CGT TGG GTG GGA CAC CCG TGG CGG
 A   S   L   V   H   R   T   A   C   Q   R   W   V   G   H   P   W   R
1413        1422        1431        1440        1449        1458

CAG CTC CCT CAG TCT TCC CTT GTC GGC CCT GAC CTN TNA CTA CAT ATG TAG NAG
 Q   L   P   Q   S   S   L   V   G   P   D   L   X   L   H   M
1467        1476        1485        1494        1503        1512

CCC GAG ACC AAA AA 3'
1521
```

FIGURE 1D

```
  1  MEASRCRLSPSGDSVFHEEMMKMRQAKLDYQRLLLEKRQR  492199
  1  M--TSKPHSDWIPYSVLDDDEGSNLRQQKLDRQQRALLEQKQK  GI 1279766
  1  M--TSKPHSDWIPYSVLDDDEGRNLRQQKLDRQRALLEQKQK  GI 1305497

41  KKRLEPFMVQPNPEARLRRAKPRASDEQTPLVNCHTPHS-  492199
 40  KKRQEPLMVQANADGRPRSRRARQSEEQAPLVESYLSSSG  GI 1279766
 40  KKRQEPLMVQANADGRPRSRRARQSEEQAPLVESYLSSSG  GI 1305497

80  ------------NVIL-----------------------  492199
 80  STSYQVQEADSIASVQLGATRPPAPASAKKSKGAAASGGG  GI 1279766
 80  STSYQVQEADSLASVQLGATRPTAPASAKRTKAAATAGGQ  GI 1305497

84  ----HGIDGPAAVLKPD-EVHAPSVSSSVVEE  492199
120  GGAPRKEKKGKHKGTSGPATLAEDKSEAQGPVQILTVGQS  GI 1279766
120  GGAARKEKKGKHKGTSGPAALAEDKSEAQGPVQILTVGQS  GI 1305497

111  DAENTVDTASKPG--------LQERLQKHDISESVNFDEE  492199
160  DHDKDAGETAAGGGAQPSGQDLRATMQRKKGISSSMSFDED  GI 1279766
160  DHAQDAGETAAGGGERPSGQDLRATMQRKGISSSMSFDED  GI 1305497

143  TDGISQSACLE------RPNSASSQNSTDTGTSGSATAA  492199
200  E-DEDENSSSSQLNSNTRPSSATSRKSIREAASAPSPAA  GI 1279766
200  EEDEEENSSSSQLNSNTRPSSATSRKSVREAASAPSPTA  GI 1305497

176  QPADNLLGDIDDLEDFVYSPAPQGVTVRCRIIRDKRGMDR  492199
239  PEPPVDIEVQDLEEFALRPAPQGITIKCRITRDKKGMDR  GI 1279766
240  PEQPVDVEVQDLEEFALRPAPQGITIKCRITRDKKGMDR  GI 1305497
```

| Pos | Sequence | ID |
|---|---|---|
| 216 | GLFPTYYMLEKEENQKIFLLAARKRKKSKTANYLISIDP | 492199 |
| 278 | GMYPTYFLHLDREDGKKVFLLAGRKRKKSKTSNYLISVDP | GI 1279766 |
| 279 | GMYPTYFLHLDREDGKKVFLLAGRKRKKSKTSNYLISVDP | GI 1305497 |
| 256 | VDLSREGESYVGKLRSNLMGTKFTVYDRGICPMKGRG-LV | 492199 |
| 318 | TDLSRGGDSYIGKLRSNLMGTKFTVYDNGVNPQKASSSTL | GI 1279766 |
| 319 | TDLSRGGDSYIGKLRSNLMGTKFTVYDNGVNPQKASSSTL | GI 1305497 |
| 295 | GAAHTRQELAAISYETNVLGFKGPRKMSVIHPGMTLNHKQ | 492199 |
| 358 | ESGTLRQELAAVCYETNVLGFKGPRKMSVIIVPGMNMVHER | GI 1279766 |
| 359 | ESGTLRQELAAVCYETNVLGFKGPRKMSVIIVPGMNMVHER | GI 1305497 |
| 335 | IPYQPQNNHDSLLSRWQNRTMENLVELHNKAPVWNSDTQS | 492199 |
| 398 | VCIRPRNEHETLLARWQNKNTESIIELQNKTPVWNDDTQS | GI 1279766 |
| 399 | VSIRPRNEHETLLARWQNKNTESIIELQNKTPVWNDDTQS | GI 1305497 |
| 375 | YVLNFRGRVTQASVKNFQIVHKNDPDYIVMQFGRVADDVF | 492199 |
| 438 | YVLNFHGRVTQASVKNFQIIHGNDPDYIVMQFGRVAEDVF | GI 1279766 |
| 439 | YVLNFHGRVTQASVKNFQIIHGNDPDYIVMQFGRVAEDVF | GI 1305497 |
| 415 | TLDYNYPLCAVQAFGIGLSSFDKRIQTLRMQELCELHRQH | 492199 |
| 478 | TMDYNYPLCALQAFAIALSSFDSKL--------------- | GI 1279766 |
| 479 | TMDYNYPLCALQAFAIALSSFDSKL--------------- | GI 1305497 |
| 455 | HSAASLVHRTACQRWVGHPWRQLPQSSLVGPDLXLHM | 492199 |
| 503 | ----AC-------------------------------E | GI 1279766 |
| 504 | ----AC-------------------------------E | GI 1305497 |

US 6,204,372 B1

DNA ENCODING A HUMAN TUBBY HOMOLOG

FIELD OF THE INVENTION

This invention relates to nucleic acid and amino acid sequences of a novel human tubby homolog and to the use of these sequences in the diagnosis, prevention, and treatment of appetite and eating disorders, especially anorexia, cachexia and obesity.

BACKGROUND OF THE INVENTION

Appetite and eating are ultimately under the control of the brain, specifically the hypothalamus and cerebral cortex; however, psychological, social, and genetic factors also affect this area of human behaviour. The cerebral cortex receives positive signals from the feeding center which is located in the ventrolateral nucleus of the hypothalamus. The feeding center stimulates eating until it is inhibited by the satiety center which is located in the ventromedial hypothalamus. Chemically, increased plasma glucose, insulin, catecholamines, and beta-adrenergic stimulation are known to inhibit the eating behaviour.

Obesity results from the disregulation of one or more of the controls or factors which influence eating. Generally, obesity is defined as an excess of adipose tissue; and clinically, it is defined as that amount of adiposity that imparts a health risk. Even mild obesity, at 20% over desirable weight according to standard height-weight charts, may increase the risk for disease and premature death.

Obesity has a major impact on human health and the US healthcare system through its effects on cardiovascular disease, diabetes mellitus, and hypertension. Although less well known, gall bladder problems; hyperlipidaemia; Alstrom, Bardet-Biedl, Cushing's, Froehlich's, and Prader-Willi syndromes; and cancers, such as craniopharyngioma and hypothalamic, pituitary, and islet cell tumors, also fall into this category. Recent studies indicate that lipophilic mutagens stored in fatty tissues such as mammary gland adipose cells may serve as the primary source for p53 mutations that result in cancers of those tissues.

The mouse obesity gene, tubby (tub), first reported as an autosomal recessive mutation has been cloned (Coleman, D. L. and E. M. Eicher (1990) J. Hered. 81:421–427; Noben-Trauth K. et al. (1996) Nature 534–38; and Kleyn, P. W. et al. (1996) Cell 85:281–90). Although different length splice variants are reported for the tub molecule, the mutant gene is abundantly expressed in hypothalamus and has a G–>T transversion which affects the 44 amino acids at the carboxyterminus. The hydrophilicity of the tub protein (pI=9.2) and the absence of signal or transmembrane motifs suggest cytosolic localization. The tub protein has two sets of serine residues separated by acidic residues which may function as a hinge, and two potential glycosylation sites, $N_{205}$ and $N_{426}$.

The tub mutation has been associated with maturity onset diabetes, insulin resistance, progressive retinal degeneration and hearing loss. Although zinc binding site motifs are not present, tub has some homology to mouse phosphodiesterase, and Noben-Trauth et al. suggest that sensory deficits may be associated with cGMP induced, phosphodiesterase mediated apoptotic activity.

Because of the numerous correlations between obesity, health, and healthcare, polypeptides related to tubby and the polynucleotides encoding them satisfy a need in the art by providing compositions useful in the diagnosis, prevention, and treatment of appetite and eating disorders, especially anorexia, cachexia, diabetes, and obesity.

SUMMARY OF THE INVENTION

The present invention features a novel human tubby homolog, hereinafter designated NHT, and characterized as having similarity to the mouse tub gene (GI 1279766, SEQ ID NO:3) and the human tub homolog (GI 1305497, SEQ ID NO:4).

Accordingly, the invention features a substantially purified NHT having the amino acid sequence shown in SEQ ID NO:1.

One aspect of the invention features isolated and substantially purified polynucleotides that encode NHT. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode NHT. The present invention also features antibodies which bind specifically to NHT, and pharmaceutical compositions comprising substantially purified NHT. The invention also features agonists and antagonists of NHT and methods for using the protein, agonists and antagonists in the treatment of appetite and eating disorders.

BRIEF DESCRIPTION OF THE FIGURES

FIGS. 1A, B, C and D show the amino acid sequence (SEQ ID NO:1) and nucleic acid sequence (SEQ ID NO:2) of NHT. The alignment was produced using MacDNASIS PRO™ software (Hitachi Software Engineering Co., Ltd., San Bruno, Calif.).

FIGS. 2A and B show the amino acid sequence alignments among NHT (SEQ ID NO:1), mouse tub gene (GI 1279766, SEQ ID NO:3) and human tub homolog (GI 1305497, SEQ ID NO:4). The alignment was produced using the multisequence alignment program of DNAS-TAR™ software (DNASTAR Inc, Madison Wis.).

DESCRIPTION OF THE INVENTION

Figure 3A:
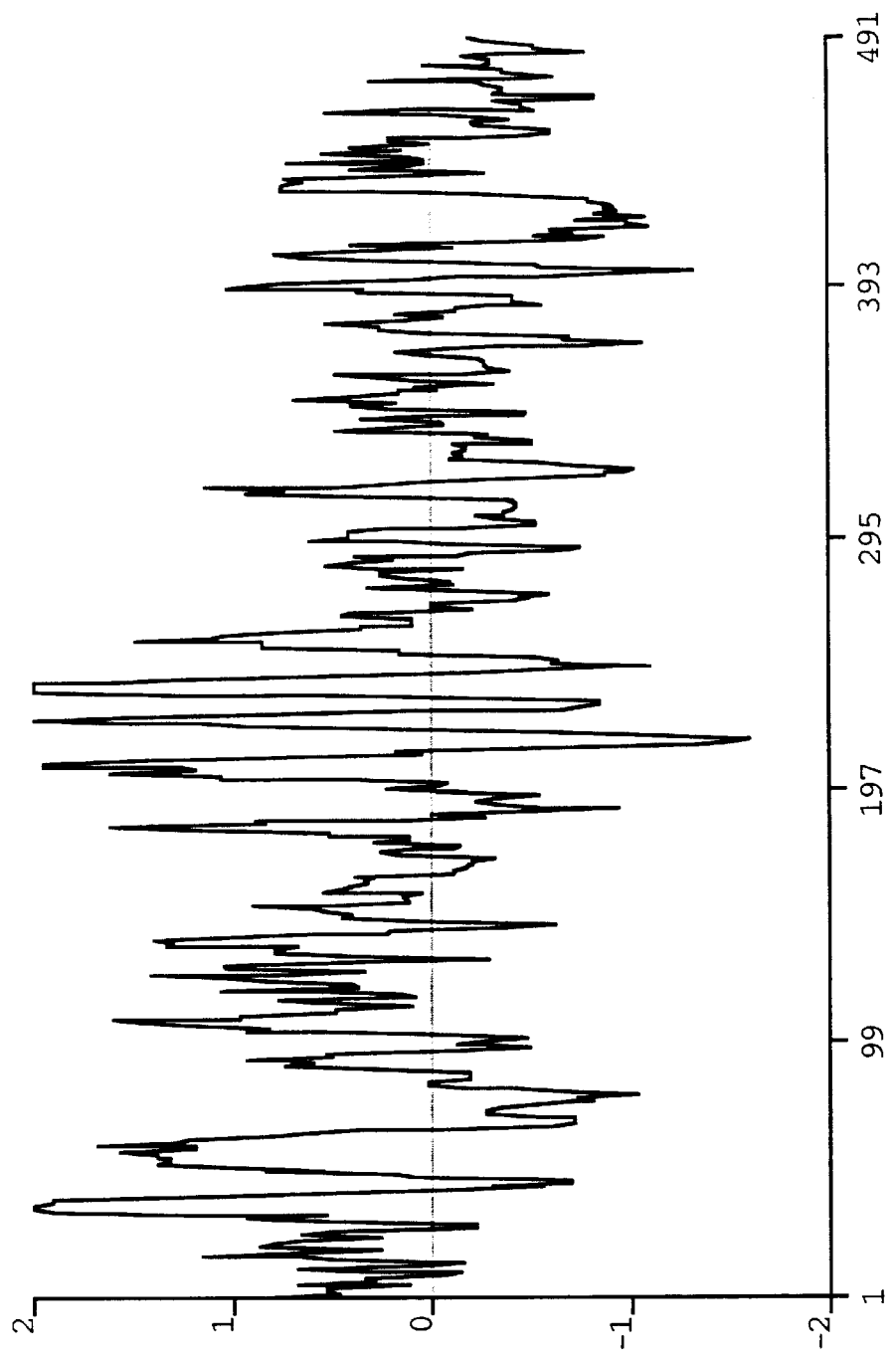
FIGS. 3A and B show the hydrophobicity plots (MacDNASIS PRO software) for NHT (SEQ ID NO:1) and mouse tub gene (SEQ ID NO:3), respectively. The positive X axis reflects amino acid position, and the negative Y axis, hydrophobicity.
Figure 3B:
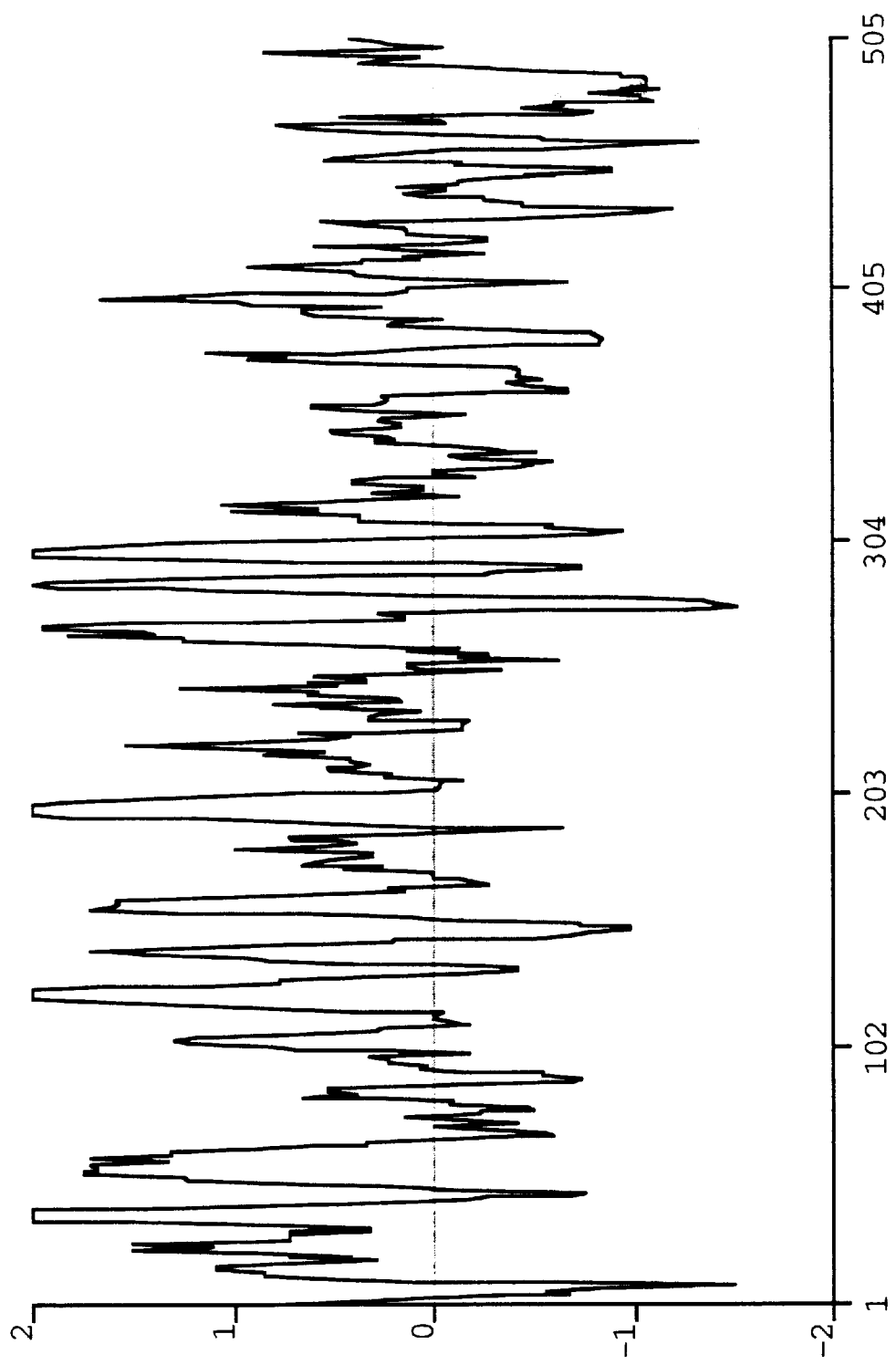

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. "Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

NHT, as used herein, refers to the amino acid sequences of substantially purified NHT obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of NHT, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic NHT, or any oligopeptide thereof, to induce a specific immune response in appropriate animals or cells and to bind with specific antibodies.

The term "agonist", as used herein, refers to a molecule which, when bound to NHT, causes a change in NHT which modulates the activity of NHT. Agonists may include proteins, nucleic acids, carbohydrates, or any other molecules which bind to NHT.

The terms "antagonist" or "inhibitor", as used herein, refer to a molecule which, when bound to NHT, blocks or modulates the biological or immunological activity of NHT. Antagonists and inhibitors may include proteins, nucleic acids, carbohydrates, or any other molecules which bind to NHT.

The term "modulate", as used herein, refers to a change or an alteration in the biological activity of NHT. Modulation may be an increase or a decrease in protein activity, a change in binding characteristics, or any other change in the biological, functional or immunological properties of NHT.

The term "mimetic", as used herein, refers to a molecule, the structure of which is developed from knowledge of the structure of NHT or portions thereof and, as such, is able to effect some or all of the actions of chemically or structurally related molecules.

The term "derivative", as used herein, refers to the chemical modification of a nucleic acid encoding NHT or the encoded NHT. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human NHT and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding NHT or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding NHT in a sample and thereby correlates with expression of the transcript from the polynucleotide encoding the protein.

"Alterations" in the polynucleotide of SEQ ID NO:2, as used herein, comprise any alteration in the sequence of polynucleotides encoding NHT including deletions, insertions, and point mutations that may be detected using hybridization assays. Included within this definition is the detection of alterations to the genomic DNA sequence which encodes NHT (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding NHT (e.g., using fluorescent in situ hybridization [FISH] to metaphase chromosomes spreads).

As used herein, the term "antibody" refers to intact molecules as well as fragments thereof, such as Fa, $F(ab')_2$, and Fv, which are capable of binding the epitopic determinant. Antibodies that bind NHT polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human tubby homolog, (NHT), the polynucleotides encoding NHT, and the use of these compositions for the diagnosis, prevention, or treatment appetite and eating disorders, especially anorexia, cachexia, diabetes, and obesity.

Nucleic acid sequence encoding the human NHT of the present invention were first identified in Incyte Clone 492199 from the HNT2 neuronal cell line cDNA library HNT2NOT01) through a computer-generated search for amino acid sequence alignments. A consensus sequence, SEQ ID NO:2, was derived from the following overlapping nucleic acid sequences: Incyte Clones 492199 (HNT2NOT01) and 539855 (LNODNOT02). In one embodiment, the invention encompasses a polypeptide comprising the amino acid sequence of SEQ ID NO:1, as shown in FIGS. 1A, B, C, and D. NHT is 491 amino acids in length and as shown in FIGS. 2A and B, has two potential N-glycosylation sites at $N_{162}$ and $N_{352}$. NHT also has potential cAMP or cGMP phosphorylation sites at $R_{241}$, and $R_{319}$. NHT has chemical and structural homology with the mouse and human tub genes (SEQ ID NO:3 and SEQ ID NO:4, respectively). In particular, NHT shares about 49% identity with the mouse and human tub proteins. NHT and the mouse tub protein show sequence related differences in their hydrophobicity plots (FIGS. 3A and B), and the isoelectric point of NHT is 8.4, slightly more neutral than that reported for mouse. NHT was expressed in five cDNA libraries; four from brain or neuronal cell lines (CORPNOT02, HNT2RAT02, HNT2NOT01, and BRAITUT22) and one from lymph node (LNODNOT02).

The invention also encompasses NHT variants. A preferred NHT variant is one having at least 80%, and more preferably 90%, amino acid sequence similarity to the NHT amino acid sequence (SEQ ID NO:1). A most preferred NHT variant is one having at least 95% amino acid sequence similarity to SEQ ID NO:1.

The invention also encompasses polynucleotides which encode NHT. Accordingly, any nucleic acid sequence which encodes the amino acid sequence of NHT can be used to generate recombinant molecules which express NHT. In a particular embodiment, the invention encompasses the polynucleotide comprising the nucleic acid sequence of SEQ ID NO:2 as shown in FIGS. 1A, B, C, and D.

It will be appreciated by those skilled in the art that as a result of the degeneracy of the genetic code, a multitude of nucleotide sequences encoding NHT, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring NHT, and all such variations are to be considered as being specifically disclosed.

Although nucleotide sequences which encode NHT and its variants are preferably capable of hybridizing to the nucleotide sequence of the naturally occurring NHT under appropriately selected conditions of stringency, it may be advantageous to produce nucleotide sequences encoding NHT or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NHT and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode NHT and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding NHT or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding NHT which are encompassed by the invention include deletions, insertions, or substitutions of different nucleotides resulting in a polynucleotide that encodes the same or a functionally equivalent NHT. The encoded protein may also contain deletions, insertions, or substitutions of amino acid residues which produce a silent change and result in a functionally equivalent NHT. Deliberate amino acid substitutions may be made on the basis of similarity in polarity, charge, solubility, hydrophobicity, hydrophilicity, and/or the amphipathic nature of the residues as long as the biological activity of NHT is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding NHT. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding NHT may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleoticle sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NHT, or fusion proteins or functional equivalents thereof, may be used in recombinant DNA molecules to direct expression of NHT in appropriate host cells. Due to the inherent degeneracy of the genetic code, other DNA sequences which encode substantially the same or a functionally equivalent amino acid sequence may be produced and these sequences may be used to clone and express NHT.

As will be understood by those of skill in the art, it may be advantageous to produce NHT-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter NHT encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding NHT may be ligated to a heterologous sequence to encode a fusion protein. For example, to screen peptide libraries for inhibitors of NHT activity, it may be useful to encode a chimeric NHT protein that can be recognized by a commercially available antibody. A fusion protein may also be engineered to contain a cleavage site located between the NHT encoding sequence and the heterologous protein sequence, so that NHT may be cleaved and purified away from the heterologous moiety.

In another embodiment, sequences encoding NHT may be synthesized, in whole or in art, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of NHT, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of NHT, or any part thereof, may be altered during direct synthesis and/or combined using chemical methods with sequences from other proteins, or any part thereof, to produce a variant polypeptide.

In order to express a biologically active NHT, the nucleotide sequences encoding NHT or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding NHT and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding NHT. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NHT, vectors based on SV40 or EBV may be used with an appropriate selectable marker.

In bacterial systems, a number of expression vectors may be selected depending upon the use intended for NHT. For example, when large quantities of NHT are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding NHT may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding NHT may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express NHT. For example, in one such system, *Autographa californica* nuclear polyhedrosis virus (AcNPV) is used as a vector to express foreign genes *Spodoptera frugiperda* cells or in Trichoplusia larvae. The sequences encoding NHT may be cloned into a non-essential region of the virus, such as the polyhedrin gene, and placed under control of the polyhedrin promoter. Successful insertion of NHT will render the polyhedrin gene inactive and produce recombinant virus lacking coat protein. The recombinant viruses may then be used to infect, for example, *S. frugiperda* cells or Trichoplusia larvae in which NHT may be expressed (Engelhard, E. K. et al. (1994) *Proc. Nat. Acad. Sci.* 91:3224–3227).

In mammalian host cells, a number of viral-based expression systems may be utilized. In cases where an adenovirus is used as an expression vector, sequences encoding NHT may be ligated into an adenovirus transcription/translation complex consisting of the late promoter and tripartite leader sequence. Insertion in a non-essential E1 or E3 region of the viral genome may be used to obtain a viable virus which is capable of expressing NHT in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding NHT. Such signals include the ATG initiation codon and adjacent sequences. In cases where sequences encoding NHT, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express NHT may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines.

These include, but are not limited to, the herpes simplex virus thymidine kinase (Wigler, M. et al. (1977) *Cell* 11:223–32) and adenine phosphoribosyltransferase (Lowy, I. et al. (1980) *Cell* 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides neomycin and G-418 (Colbere-Garapin, F. et al (1981) *J. Mol. Biol.* 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding NHT is inserted within a marker gene sequence, recombinant cells containing sequences encoding NHT can be identified by the absence of marker gene function. Alternatively, a marker gene can be placed in tandem with a sequence encoding NHT under the control of a single promoter. Expression of the marker gene in response to induction or selection usually indicates expression of the tandem gene as well.

Alternatively, host cells which contain the nucleic acid sequence encoding NHT and express NHT may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding NHT can be detected by DNA-DNA or DNA-RNA hybridization or amplification using probes or portions or fragments of polynucleotides encoding NHT. Nucleic acid amplification based assays involve the use of oligonucleotides or oligomers based on the sequences encoding NHT to detect transformants containing DNA or RNA encoding NHT. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of NHT, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on NHT is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NHT include oligolabeling, nick translation, end-labeling or PCR amplification using a labeled nucleotide. Alternatively, the sequences encoding NHT, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding NHT may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode NHT may be designed to contain signal sequences which direct secretion of NHT through a prokaryotic or eukaryotic cell membrane. Other recombinant constructions may be used to join sequences encoding NHT to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and NHT may be used to facilitate purification. One such expression vector provides for expression of a fusion protein containing NHT and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying NHT from the fusion protein. A discussion of vectors which contain fusion proteins is provided in Kroll, D. J. et al. (1993; DNA Cell Biol. 12:441–453).

In addition to recombinant production, fragments of NHT may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of NHT may be chemically synthesized separately and combined using chemical methods to produce the full length molecule.

Therapeutics

NHT shares 49% chemical and structural homology with mouse and human tub genes and is expressed in four different brain libraries and in one lymph node library. Therefore, expression of NHT appears to be associated with mammalian appetite and eating disorders.

In one embodiment, NHT or a fragment or derivative thereof may be administered to a subject to inhibit appetite or overeating, and in particular to treat or prevent a disorder which is associated with overeating. Such disorders may include cardiovascular diseases such as arteriosclerosis, atheroschlerosis, and hypertension, autoimmune or genetic disorders such as asthma, fatty liver or pancreas, hypoglycemia, hyperglycemia, and diabetes mellitus, gall bladder disease; hyperlipidaemia; Alstrom, Bardet-Biedl, Cushing's, Froehlich's, and Prader-Willi syndromes; sleep apnea; and adenocarcinomas, leukemias, lymphomas, melanomas, or sarcomas, particularly cancers such as craniopharyngioma, hypothalmic, pituitary, and islet cell tumors, and adenocarcinomas of the brain, breast, gall bladder, liver, pancreas, and prostate.

In another embodiment, a vector capable of expressing NHT, or a fragment or a derivative thereof, may be administered to a subject to treat or prevent a disorder associated with overeating including, but not limited to, those listed above.

In another embodiment, agonists which are specific for NHT may be used to stimulate or prolong the activity of NHT and may be administered to a subject to treat or prevent a disorder associated with overeating including, but not limited to, those listed above.

In another embodiment, antagonists or inhibitors of NHT may be administered to stimulate appetite or eating, and in particular, to treat or prevent an eating disorder. Such a disorder may include, but is not limited to, amenorrhea, anorexia nervosa, bulimia nervosa, cachexia, and loss of appetite associated with chemotherapy, clinical depression, or grieving.

In another embodiment, antibodies which are specific for NHT may be used directly as an antagonist, or indirectly as a targeting or delivery mechanism for bringing a pharmaceutical agent to a subject with an eating disorder including, but not limited to, those listed above.

In another embodiment, a vector expressing antisense of the polynucleotide encoding NHT may be administered to a subject to to treat or prevent an eating disorder including, but not limited to, those listed above.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of NHT may be produced using methods which are generally known in the art. In particular, purified NHT may be used to produce antibodies or to screen libraries of pharmaceutical agents to identify those which specifically bind NHT.

Antibodies to NHT may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies to NHT, various hosts including goats, rabbits, rats, mice, humans, and others, may be immunized by injection with NHT or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to NHT have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of NHT amino acids may to be fused with those of another protein such as keyhole limpet hemocyanin and antibody produced against the chimeric molecule.

Monoclonal antibodies to NHT may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce NHT-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for NHT may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between NHT and its specific antibody. A two-site, monoclonal-based immunoassay utilizing monoclonal antibodies reactive to two non-interfering NHT epitopes is preferred, but a competitive binding assay may also be employed (Maddox, supra).

In another embodiment of the invention, the polynucleotides encoding NHT, or any fragment thereof, or antisense molecules, may be used for therapeutic purposes. In one aspect, antisense to the polynucleotide encoding NHT may be used in situations in which it would be desirable to block the transcription of the mRNA. In particular, cells may be transformed with sequences complementary to polynucleotides encoding NHT. Thus, antisense molecules may be used to modulate NHT activity, or to achieve regulation of gene function. Such technology is now well known in the art, and sense or antisense oligomers or larger fragments, can be designed from various locations along the coding or control regions of sequences encoding NHT.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding NHT. These techniques are described both in Sambrook et al. (supra) and in Ausubel et al. (supra).

Genes encoding NHT can be turned off by transforming a cell or tissue with expression vectors which express high levels of a polynucleotide or fragment thereof which encodes NHT. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding NHT, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NHT.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NHT. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NHT, antibodies to NHT, mimetics, agonists, antagonists, or inhibitors of NHT. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of NHT, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example NHT or fragments thereof, antibodies of NHT, agonists, antagonists or inhibitors of NHT, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50(the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind NHT may be used for the diagnosis of conditions or diseases characterized by expression of NHT, or in assays to monitor patients being treated with NHT, agonists, antagonists or inhibitors. The antibodies useful for diagnostic purposes may be prepared in the same manner as those described above for therapeutics. Diagnostic assays for NHT include methods which utilize the antibody and a label to detect NHT in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring NHT are known in the art and provide a basis for diagnosing altered or abnormal levels of NHT expression. Normal or standard values for NHT expression are established by combining body fluids or cell extracts taken from normal mammalian subjects, preferably human, with antibody to NHT under conditions suitable for complex formation The amount of standard complex formation may be quantified by various methods, but preferably by photometric, means. Quantities of NHT expressed in subject, control and disease, samples from biopsied tissues are compared with the standard values. Deviation between standard and subject values establishes the parameters for diagnosing disease.

In another embodiment of the invention, the polynucleotides encoding NHT may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of NHT may be correlated with disease. The diagnostic assay may be used to distinguish between absence, presence, and excess expression of NHT, and to monitor regulation of NHT levels during therapeutic intervention.

In one aspect, hybridization with PCR probes which are capable of detecting polynucleotide sequences, including genomic sequences, encoding NHT or closely related molecules, may be used to identify nucleic acid sequences which encode NHT. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding NHT, alleles, or related sequences.

Probes may also be used for the detection of related sequences, and should preferably contain at least 50% of the nucleotides from any of the NHT encoding sequences. The hybridization probes of the subject invention may be DNA or RNA and derived from the nucleotide sequence of SEQ ID NO:2 or from genomic sequence including promoter, enhancer elements, and introns of the naturally occurring NHT.

Means for producing specific hybridization probes for DNAs encoding NHT include the cloning of nucleic acid sequences encoding NHT or NHT derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding NHT may be used for the diagnosis or monitoring appetite and eating disorders, especially those associated with amenorrhea; anorexia nervosa; bulimia nervosa; cachexia; loss of appetite associated with chemotherapy, clinical depression, or grieving; cardiovascular diseases such as arteriosclerosis, ateroschlerosis, and hypertension, autoimmune or genetic disorders such as asthma, fatty liver or pancreas, hypoglycemia, hyperglycemia, and diabetes mellitus, gall bladder disease; hyperlipidaemia; strom, Bardet-Biedl, Cushing's, Froehlich's, and Prader-Willi syndromes; sleep apnea; and adenocarcinomas, leukemias, lymphomas, melanomas, or sarcomas, particularly aniopharyngioma, hypothalmic, pituitary, and islet cell tumors, and adenocarcinomas of the brain, breast, gall bladder, liver, pancreas, and prostate.

The polynucleotide sequences encoding NHT may be used in Southern or northern analysis, dot blot, or other membrane-based technologies; in PCR technologies; or in dip stick, pin, ELISA or chip assays utilizing fluids or tissues from patient biopsies to detect altered NHT expression. Such qualitative or quantitative methods are well known in the art.

In a particular aspect, the nucleotide sequences encoding NHT may be useful in assays that detect activation or induction of various cancers, particularly those mentioned above. The nucleotide sequences encoding NHT may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NHT in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NHT, a normal or standard profile for expression is established. This may be accomplished by combining body fluids or cell extracts taken from normal subjects, either animal or human, with a sequence, or a fragment thereof, which encodes NHT, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NHT may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NHT include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode NHT may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding NHT on a physical chromosomal map and a specific disease , or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) *Nature* 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, NHT, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between NHT and the agent being tested, may be measured.

Another technique for drug screening which may be used provides for high throughput screening of compounds having suitable binding affinity to the protein of interest as described in published PCT application WO84/03564. In this method, as applied to NHT large numbers of different small test compounds are synthesized on a solid substrate, such as plastic pins or some other surface. The test compounds are reacted with NHT, or fragments thereof, and washed. Bound NHT is then detected by methods well known in the art. Purified NHT can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NHT specifically compete with a test compound for binding NHT. In this manner, the antibodies can be used to detect the presence of any peptide which shares one or more antigenic determinants with NHT.

In additional embodiments, the nucleotide sequences which encode NHT may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I HNT2NOT01 cDNA Library Construction

The hNT2 cell line exhibits characteristics of a committed neuronal precursor cell which is still at an early stage of development. The cDNA library (HNT2NOT01; Cat. No. 937230) was prepared from untreated hNT2 cell line by Stratagene (La Jolla, Calif.).

cDNAs were primed using oligo d(T) and size fractionated to isolate fragments of 500 bp and larger. Synthetic adapter oligonuclcotides were ligated onto the cDNA molecules enabling them to be inserted into the Uni-ZAP™ vector system (Stratagene).

The quality of the cDNA library was screened using DNA probes, and then, the pBluescript™ phagemid (Stratagene) was excised. Subsequently, the phagemid was transfected into *E. coli* host strain XL1-Blue™ (Stratagene). Alternative unidirectional vectors include, but are not limited to, pcDNAI (Invitrogen, San Diego Calif.) and pSH1ox-1 (Novagen, Madison Wis.).

II Isolation of cDNA Clones

The phagemids containing individual cDNA clones were isolated with the Miniprep Kit (Cat. No. 77468; Advanced Genetic Technologies Corp., Gaithersburg Md.). This kit has a 96-well format and provides enough reagents for 960 purifications. The recommended protocol was employed except for the following changes. First, the 96 wells were each filled with only 1 ml of sterile terrific broth with carbenicillin at 25 mg/L and glycerol at 0.4%. After the wells were inoculated, the bacteria were cultured for 24 hours and lysed with 60 μl of lysis buffer. A centrifugation at 2900 rpm for 5 minutes was performed before the contents of the block were added to the primary filter plate. The optional step of adding isopropanol to TRIS buffer was not routinely performed. After the last step in the protocol, samples were transferred to a Beckman 96-well block for storage.

Alternatively, the in vivo excision process, in which the host bacterial strain is co-infected with both the library phage and an f1 helper phage, was used to harvest the phagemid. Polypeptides or enzymes derived from both the library-containing phage and the helper phage nicked the DNA, initiated new DNA synthesis from defined sequences on the target DNA, and created a smaller, single stranded circular phagemid DNA molecule. The circular molecule included all DNA sequences of the pBluescript phagemid and the cDNA insert. When the phagemid DNA was released from the cells, it was purified, and used to reinfect fresh host cells (SOLR, Stratagene) which produced double-stranded DNA. Because the phagemid carries the gene for §-lactamase, the newly transformed bacteria were selected on medium containing ampicillin.

Phagemid DNA may also be purified using the QIAWELL-8 Plasmid purification system (QIAGEN Inc, Chatsworth Calif.). This product provides a convenient, rapid and reliable high-throughput method for lysing the bacterial cells and isolating highly purified phagemid DNA. The DNA is eluted from the purification resin and prepared for DNA sequencing and other analytical manipulations.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) *J. Mol. Evol.* 36:290–300;

Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\ \text{sequence identity} \times \%\ \text{maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding NHT occurs. Abundance and percent abundance are also reported. Abundance directly reflects the number of times a particular transcript is represented in a cDNA library, and percent abundance is abundance divided by the total number of sequences examined in the cDNA library.

V Extension of NHT Polynucleotide Sequences

The nucleic acid sequence of Incyte Clone 492199 is used to design oligonucleotide primers for extending a partial nucleotide sequence to full length. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 $\mu$l aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick Kit (Qiagen Inc.). After recovery of the DNA, Klenow enzyme is used to trim single-stranded, nucleotide overhangs creating blunt ends which facilitate religation and cloning.

After ethanol precipitation, the products are redissolved in 13 $\mu$l of ligation buffer, 1 $\mu$l T4-DNA ligase (15 units) and 1 $\mu$l T4 polynucleotide kinase are added, and the mixture is incubated at room temperature for 2–3 hours or overnight at 16° C. Competent E. coli cells (in 40 $\mu$l of appropriate media) are transformed with 3 $\mu$l of ligation mixture and cultured in 80 $\mu$l of SOC medium (Sambrook et al., supra). After incubation for one hour at 37° C., the whole transformation mixture is plated on Luria Bertani (LB)-agar (Sambrook et al., supra) containing 2x Carb. The following day, several colonies are randomly picked from each plate and cultured in 150 $\mu$l of liquid LB/2x Carb medium placed in an individual well of an appropriate, commercially-available, sterile 96-well microtiter plate. The following day, 5 $\mu$l of each overnight culture is transferred into a non-sterile 96-well plate and after dilution 1:10 with water, 5 $\mu$l of each sample is transferred into a PCR array.

For PCR amplification, 18 $\mu$l of concentrated PCR reaction mix (3.3x) containing 4 units of rTth DNA polymerase, a vector primer, and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

In like manner, the nucleotide sequence of SEQ ID NO:2 can be used to obtain 5' regulatory sequences using the procedure above, oligonucleotides designed for 5' extension, and an appropriate genomic library.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bg1II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Complementary Nucleic Acid Molecules

Antisense molecules or nucleic acid sequences complementary to the NHT-encoding sequence, or any part thereof, are used to inhibit in vivo or in vitro expression of naturally occurring NHT. Although use of antisense oligonucleotides, comprising about 20 base-pairs, is specifically described, essentially the same procedure is used with larger cDNA fragments. An oligonucleotide based on the coding sequences of NHT, as shown in FIGS. 1A and B, is used to inhibit expression of naturally occurring NHT. The complementary oligonucleotide is designed from the most unique 5' sequence as shown in FIGS. 1A and B and used either to inhibit transcription by preventing promoter binding to the upstream nontranslated sequence or translation of an NHT-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A and B.

VIII Expression of NHT

Expression of NHT is accomplished by subcloning the cDNAs into appropriate vectors and transforming the vectors into host cells. In this case, the cloning vector, previously used for the generation of the cDNA library is used to express NHT in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of NHT into the bacterial growth media which can be used directly in the following assay for activity.

IX Demonstration of NHT Activity

The ability of NHT to stimulate appetite and eating can be tested in mice. The amount of food consumed per day, the average weight gain in a particular time period, the adipose deposition in females versus males and the differences in weight gain between litter mates receiving or not receiving the protein can be compared.

X Production of NHT Specific Antibodies

NHT that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring NHT Using Specific Antibodies

Naturally occurring or recombinant NHT is substantially purified by immunoaffinity chromatography using antibodies specific for NHT. An immunoaffinity column is constructed by covalently coupling NHT antibody to an activated chromatographic resin, such as CnBr-activated Sepharose (Pharmacia & Upjohn). After the coupling, the resin is blocked and washed according to the manufacturer's instructions.

Media containing NHT is passed over the immunoaffinity column, and the column is washed under conditions that allow the preferential absorbance of NHT (e.g., high ionic strength buffers in the presence of detergent). The column is eluted under conditions that disrupt antibody/NHT binding (eg, a buffer of pH 2–3 or a high concentration of a chaotrope, such as urea or thiocyanate ion), and NHT is collected.

XII Identification of Molecules Which Interact with NHT

NHT or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled NHT, washed and any wells with labeled NHT complex are assayed. Data obtained using different concentrations of NHT are used to calculate values for the number, affinity, and association of NHT with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEQ ID NO:1.

2. An isolated and purified polynucleotide which hybridizes under stringent conditions to the polynucleotide of claim 1.

3. A hybridization probe comprising the polynucleotide of claim 1 and a detectable label.

4. An isolated and purified polynucleotide comprising SEQ ID NO:2.

5. An isolated and purified polynucleotide sequence which is fully complementary to the polynucleotide of claim 1.

6. A hybridization probe comprising the polynucleotide of claim 5 and a detectable label.

7. An expression vector containing the polynucleotide of claim 1.

8. A host cell containing the expression vector of claim 7.

9. A method for producing a polypeptide comprising the amino acid sequence of SEQ ID NO:1, the method comprising the steps of:

a) culturing the host cell of claim 8 under conditions suitable for the expression of the polypeptide; and b) recovering the polypeptide from the host cell culture.

* * * * *

```
                        SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 491 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (A) LIBRARY: HNT2NOT01
         (B) CLONE: Concensus (xi) SEQUENCE DESCRIPTION: SEQ ID NO:1:

Met Glu Ala Ser Arg Cys Arg Leu Ser Pro Ser Gly Asp Ser Val Phe
    1               5                  10                  15

His Glu Glu Met Met Lys Met Arg Gln Ala Lys Leu Asp Tyr Gln Arg
                    20                  25                  30

Leu Leu Leu Glu Lys Arg Gln Arg Lys Lys Arg Leu Glu Pro Phe Met
                35                  40                  45

Val Gln Pro Asn Pro Glu Ala Arg Leu Arg Arg Ala Lys Pro Arg Ala
        50                  55                  60

Ser Asp Glu Gln Thr Pro Leu Val Asn Cys His Thr Pro His Ser Asn
    65                  70                  75                  80

Val Ile Leu His Gly Ile Asp Gly Pro Ala Ala Val Leu Lys Pro Asp
                    85                  90                  95

Glu Val His Ala Pro Ser Val Ser Ser Val Val Glu Glu Asp Ala
                    100                 105                 110

Glu Asn Thr Val Asp Thr Ala Ser Lys Pro Gly Leu Gln Glu Arg Leu
                    115                 120                 125

Gln Lys His Asp Ile Ser Glu Ser Val Asn Phe Asp Glu Glu Thr Asp
        130                 135                 140

Gly Ile Ser Gln Ser Ala Cys Leu Glu Arg Pro Asn Ser Ala Ser Ser
    145                 150                 155                 160

Gln Asn Ser Thr Asp Thr Gly Thr Ser Gly Ser Ala Thr Ala Ala Gln
                    165                 170                 175

Pro Ala Asp Asn Leu Leu Gly Asp Ile Asp Asp Leu Glu Asp Phe Val
                    180                 185                 190

Tyr Ser Pro Ala Pro Gln Gly Val Thr Val Arg Cys Arg Ile Ile Arg
                    195                 200                 205
```

-continued

```
Asp Lys Arg Gly Met Asp Arg Gly Leu Phe Pro Thr Tyr Tyr Met Tyr
            210                 215                 220

Leu Glu Lys Glu Glu Asn Gln Lys Ile Phe Leu Leu Ala Ala Arg Lys
225                 230                 235                 240

Arg Lys Lys Ser Lys Thr Ala Asn Tyr Leu Ile Ser Ile Asp Pro Val
                245                 250                 255

Asp Leu Ser Arg Glu Gly Glu Ser Tyr Val Gly Lys Leu Arg Ser Asn
                260                 265                 270

Leu Met Gly Thr Lys Phe Thr Val Tyr Asp Arg Gly Ile Cys Pro Met
            275                 280                 285

Lys Gly Arg Gly Leu Val Gly Ala Ala His Thr Arg Gln Glu Leu Ala
290                 295                 300

Ala Ile Ser Tyr Glu Thr Asn Val Leu Gly Phe Lys Gly Pro Arg Lys
305                 310                 315                 320

Met Ser Val Ile Ile Pro Gly Met Thr Leu Asn His Lys Gln Ile Pro
                325                 330                 335

Tyr Gln Pro Gln Asn Asn His Asp Ser Leu Leu Ser Arg Trp Gln Asn
                340                 345                 350

Arg Thr Met Glu Asn Leu Val Glu Leu His Asn Lys Ala Pro Val Trp
            355                 360                 365

Asn Ser Asp Thr Gln Ser Tyr Val Leu Asn Phe Arg Gly Arg Val Thr
370                 375                 380

Gln Ala Ser Val Lys Asn Phe Gln Ile Val His Lys Asn Asp Pro Asp
385                 390                 395                 400

Tyr Ile Val Met Gln Phe Gly Arg Val Ala Asp Val Phe Thr Leu
                405                 410                 415

Asp Tyr Asn Tyr Pro Leu Cys Ala Val Gln Ala Phe Gly Ile Gly Leu
                420                 425                 430

Ser Ser Phe Asp Lys Arg Ile Gln Thr Leu Arg Met Gln Glu Leu Cys
            435                 440                 445

Glu Leu His Arg Gln His His Ser Ala Ala Ser Leu Val His Arg Thr
            450                 455                 460

Ala Cys Gln Arg Trp Val Gly His Pro Trp Arg Gln Leu Pro Gln Ser
465                 470                 475                 480

Ser Leu Val Gly Pro Asp Leu Xaa Leu His Met
                485                 490
```

(2) INFORMATION FOR SEQ ID NO:2:

(i) SEQUENCE CHARACTERISTICS:
        (A) LENGTH: 1525 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: HNT2NOT01
        (B) CLONE: Concensus (xi) SEQUENCE DESCRIPTION: SEQ ID NO:2:

```
GCACGAGGTG GGGGCTTTCC TCGGTGGCGG GCATGGAGGC TTCGCGCTGC CGGCTCAGTC    60

CCAGCGGCGA CAGTGTCTTC CATGAAGAAA TGATGAAGAT GCGACAGGCT AAGCTGGATT   120

ATCAGAGGCT ACTACTTGAG AAGAGGCAAA GGAAAAAGCG CCTTGAGCCA TTTATGGTGC   180

AGCCCAATCC AGAAGCCAGG CTACGTCGGG CAAAGCCAAG GGCCAGTGAT GAGCAGACTC   240
```

-continued

```
CCTTGGTGAA CTGTCATACT CCCCACAGCA ATGTCATCTT ACATGGTATT GATGGTCCAG      300

CTGCTGTCCT GAAACCAGAC GAAGTTCATG CTCCATCAGT AAGCTCCTCT GTTGTGGAAG      360

AAGATGCTGA AAACACCGTG GATACTGCTT CCAAGCCAGG ACTTCAGGAG CGTCTCCAAA      420

AGCATGATAT CTCTGAAAGT GTGAACTTCG ATGAGGAGAC TGATGGAATA TCCCAGTCAG      480

CATGTTTAGA AAGACCCAAT TCTGCATCAA GCCAGAATTC AACCGATACA GGCACTTCCG      540

GTTCTGCTAC TGCCGCCCAA CCAGCTGATA ACCTCCTGGG AGACATAGAC GACCTGGAGG      600

ACTTTGTGTA TAGTCCTGCC CCTCAAGGTG TCACAGTAAG ATGTCGGATA ATCCGGGATA      660

AAAGGGGAAT GGATCGGGGT CTCTTCCCCA CCTACTATAT GTACTTGGAA AAAGAAGAAA      720

ATCAGAAGAT ATTTCTTCTT GCAGCTAGAA AGCGGAAAAA GAGCAAAACA GCCAACTACC      780

TTATCTCCAT TGATCCAGTT GATTTATCTC GTGAAGGAGA AAGTTATGTC GGCAAGCTTA      840

GATCCAACCT CATGGGGACC AAGTTTACAG TTTATGACCG TGGCATCTGC CCCATGAAGG      900

GCCGGGGTTT GGTAGGAGCG GCCCACACCC GGCAGGAGCT GGCTGCCATC TCCTATGAAA      960

CAAACGTACT TGGATTTAAA GGTCCTAGGA AAATGTCTGT GATCATTCCT GGAATGACAC     1020

TGAATCATAA GCAGATCCCC TATCAGCCAC AAAACAACCA TGACAGTTTG CTCTCAAGGT     1080

GGCAGAACAG AACTATGAAA AATCTGGTTG AGCTGCACAA CAAGGCCCCC GTCTGGAACA     1140

GTGACACTCA GTCCTATGTC CTCAACTTCC GTGGCCGGGT CACTCAGGCG TCTGTGAAGA     1200

ACTTCCAGAT AGTCCACAAA AATGACCCTG ATTATATAGT CATGCAGTTT GGACGTGTGG     1260

CAGATGACGT GTTCACACTG GATTACAACT ACCCACTTTG TGCAGTACAG GCCTTTGGCA     1320

TCGGTCTTTC TAGCTTTGAC AAACGTATCC AAACCTTGAG AATGCAGGAG CTCTGTGAGC     1380

TCCACCGTCA GCACCATTCA GCTGCATCCC TTGTGCACAG GACTGCCTGC CAGCGTTGGG     1440

TGGGACACCC GTGGCGGCAG CTCCCTCAGT CTTCCCTTGT CGGCCCTGAC CTNTNACTAC     1500

ATATGTAGNA GCCCGAGACC AAAAA                                            1525
```

(2) INFORMATION FOR SEQ ID NO:3:

(i) SEQUENCE CHARACTERISTICS:
        (A) LENGTH: 505 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1279766

(xi) SEQUENCE DESCRIPTION: SEQ ID NO:3:

```
Met Thr Ser Lys Pro His Ser Asp Trp Ile Pro Tyr Ser Val Leu Asp
 1               5                  10                  15

Asp Glu Gly Ser Asn Leu Arg Gln Gln Lys Leu Asp Arg Gln Arg Ala
            20                  25                  30

Leu Leu Glu Gln Lys Gln Lys Lys Arg Gln Glu Pro Leu Met Val
        35                  40                  45

Gln Ala Asn Ala Asp Gly Arg Pro Arg Ser Arg Arg Ala Arg Gln Ser
    50                  55                  60

Glu Glu Gln Ala Pro Leu Val Glu Ser Tyr Leu Ser Ser Gly Ser
65                  70                  75                  80

Thr Ser Tyr Gln Val Gln Glu Ala Asp Ser Ile Ala Ser Val Gln Leu
            85                  90                  95
```

-continued

```
Gly Ala Thr Arg Pro Pro Ala Pro Ser Ala Lys Lys Ser Lys Gly
            100                 105                 110
Ala Ala Ala Ser Gly Gly Gln Gly Gly Ala Pro Arg Lys Glu Lys Lys
        115                 120                 125
Gly Lys His Lys Gly Thr Ser Gly Pro Ala Thr Leu Ala Glu Asp Lys
    130                 135                 140
Ser Glu Ala Gln Gly Pro Val Gln Ile Leu Thr Val Gly Gln Ser Asp
145                 150                 155                 160
His Asp Lys Asp Ala Gly Glu Thr Ala Ala Gly Gly Ala Gln Pro
                165                 170                 175
Ser Gly Gln Asp Leu Arg Ala Thr Met Gln Arg Lys Gly Ile Ser Ser
            180                 185                 190
Ser Met Ser Phe Asp Glu Asp Glu Asp Glu Asp Glu Asn Ser Ser Ser
        195                 200                 205
Ser Ser Gln Leu Asn Ser Asn Thr Arg Pro Ser Ser Ala Thr Ser Arg
    210                 215                 220
Lys Ser Ile Arg Glu Ala Ala Ser Ala Pro Ser Ala Ala Pro Glu
225                 230                 235                 240
Pro Pro Val Asp Ile Glu Val Gln Asp Leu Glu Glu Phe Ala Leu Arg
                245                 250                 255
Pro Ala Pro Gln Gly Ile Thr Ile Lys Cys Arg Ile Thr Arg Asp Lys
            260                 265                 270
Lys Gly Met Asp Arg Gly Met Tyr Pro Thr Tyr Phe Leu His Leu Asp
        275                 280                 285
Arg Glu Asp Gly Lys Lys Val Phe Leu Leu Ala Gly Arg Lys Arg Lys
    290                 295                 300
Lys Ser Lys Thr Ser Asn Tyr Leu Ile Ser Val Asp Pro Thr Asp Leu
305                 310                 315                 320
Ser Arg Gly Gly Asp Ser Tyr Ile Gly Lys Leu Arg Ser Asn Leu Met
                325                 330                 335
Gly Thr Lys Phe Thr Val Tyr Asp Asn Gly Val Asn Pro Gln Lys Ala
            340                 345                 350
Ser Ser Ser Thr Leu Glu Ser Gly Thr Leu Arg Gln Glu Leu Ala Ala
        355                 360                 365
Val Cys Tyr Glu Thr Asn Val Leu Gly Phe Lys Gly Pro Arg Lys Met
    370                 375                 380
Ser Val Ile Val Pro Gly Met Asn Met Val His Glu Arg Val Cys Ile
385                 390                 395                 400
Arg Pro Arg Asn Glu His Glu Thr Leu Leu Ala Arg Trp Gln Asn Lys
                405                 410                 415
Asn Thr Glu Ser Ile Ile Glu Leu Gln Asn Lys Thr Pro Val Trp Asn
            420                 425                 430
Asp Asp Thr Gln Ser Tyr Val Leu Asn Phe His Gly Arg Val Thr Gln
        435                 440                 445
Ala Ser Val Lys Asn Phe Gln Ile Ile His Gly Asn Asp Pro Asp Tyr
    450                 455                 460
Ile Val Met Gln Phe Gly Arg Val Ala Glu Asp Val Phe Thr Met Asp
465                 470                 475                 480
Tyr Asn Tyr Pro Leu Cys Ala Leu Gln Ala Phe Ala Ile Ala Leu Ser
                485                 490                 495
Ser Phe Asp Ser Lys Leu Ala Cys Glu
            500                 505
```

(2) INFORMATION FOR SEQ ID NO:4:

(i) SEQUENCE CHARACTERISTICS:
        (A) LENGTH: 506 amino acids
        (B) TYPE: amino acid
        (C) STRANDEDNESS: single
        (D) TOPOLOGY: linear (ii) MOLECULE TYPE: protein (vii) IMMEDIATE SOURCE:
        (A) LIBRARY: GenBank
        (B) CLONE: 1305497

(xi) SEQUENCE DESCRIPTION: SEQ ID NO:4:

```
Met Thr Ser Lys Pro His Ser Asp Trp Ile Pro Tyr Ser Val Leu Asp
 1               5                  10                  15

Asp Glu Gly Arg Asn Leu Arg Gln Gln Lys Leu Asp Arg Gln Arg Ala
            20                  25                  30

Leu Leu Glu Gln Lys Gln Lys Lys Arg Gln Glu Pro Leu Met Val
        35                  40                  45

Gln Ala Asn Ala Asp Gly Arg Pro Arg Ser Arg Ala Arg Gln Ser
 50                  55                  60

Glu Glu Gln Ala Pro Leu Val Glu Ser Tyr Leu Ser Ser Gly Ser
 65                  70                  75                  80

Thr Ser Tyr Gln Val Gln Glu Ala Asp Ser Leu Ala Ser Val Gln Leu
                85                  90                  95

Gly Ala Thr Arg Pro Thr Ala Pro Ala Ser Ala Lys Arg Thr Lys Ala
            100                 105                 110

Ala Ala Thr Ala Gly Gly Gln Gly Gly Ala Ala Arg Lys Glu Lys Lys
            115                 120                 125

Gly Lys His Lys Gly Thr Ser Gly Pro Ala Ala Leu Ala Glu Asp Lys
130                 135                 140

Ser Glu Ala Gln Gly Pro Val Gln Ile Leu Thr Val Gly Gln Ser Asp
145                 150                 155                 160

His Ala Gln Asp Ala Gly Glu Thr Ala Ala Gly Gly Gly Glu Arg Pro
                165                 170                 175

Ser Gly Gln Asp Leu Arg Ala Thr Met Gln Arg Lys Gly Ile Ser Ser
            180                 185                 190

Ser Met Ser Phe Asp Glu Asp Glu Asp Glu Glu Asn Ser Ser
            195                 200                 205

Ser Ser Ser Gln Leu Asn Ser Asn Thr Arg Pro Ser Ser Ala Thr Ser
210                 215                 220

Arg Lys Ser Val Arg Glu Ala Ala Ser Ala Pro Ser Pro Thr Ala Pro
225                 230                 235                 240

Glu Gln Pro Val Asp Val Glu Val Gln Asp Leu Glu Glu Phe Ala Leu
                245                 250                 255

Arg Pro Ala Pro Gln Gly Ile Thr Ile Lys Cys Arg Ile Thr Arg Asp
            260                 265                 270

Lys Lys Gly Met Asp Arg Gly Met Tyr Pro Thr Tyr Phe Leu His Leu
            275                 280                 285

Asp Arg Glu Asp Gly Lys Lys Val Phe Leu Leu Ala Gly Arg Lys Arg
        290                 295                 300

Lys Lys Ser Lys Thr Ser Asn Tyr Leu Ile Ser Val Asp Pro Thr Asp
305                 310                 315                 320

Leu Ser Arg Gly Gly Asp Ser Tyr Ile Gly Lys Leu Arg Ser Asn Leu
                325                 330                 335
```

```
Met Gly Thr Lys Phe Thr Val Tyr Asp Asn Gly Val Asn Pro Gln Lys
            340                 345                 350

Ala Ser Ser Ser Thr Leu Glu Ser Gly Thr Leu Arg Gln Glu Leu Ala
            355                 360                 365

Ala Val Cys Tyr Glu Thr Asn Val Leu Gly Phe Lys Gly Pro Arg Lys
            370                 375                 380

Met Ser Val Ile Val Pro Gly Met Asn Met Val His Glu Arg Val Ser
385                 390                 395                 400

Ile Arg Pro Arg Asn Glu His Glu Thr Leu Leu Ala Arg Trp Gln Asn
                405                 410                 415

Lys Asn Thr Glu Ser Ile Ile Glu Leu Gln Asn Lys Thr Pro Val Trp
            420                 425                 430

Asn Asp Asp Thr Gln Ser Tyr Val Leu Asn Phe His Gly Arg Val Thr
            435                 440                 445

Gln Ala Ser Val Lys Asn Phe Gln Ile Ile His Gly Asn Asp Pro Asp
            450                 455                 460

Tyr Ile Val Met Gln Phe Gly Arg Val Ala Glu Asp Val Phe Thr Met
465                 470                 475                 480

Asp Tyr Asn Tyr Pro Leu Cys Ala Leu Gln Ala Phe Ala Ile Ala Leu
                485                 490                 495

Ser Ser Phe Asp Ser Lys Leu Ala Cys Glu
            500                 505
```